United States Patent [19]

Yamada et al.

[11] 4,242,452

[45] * Dec. 30, 1980

[54] PROCESS FOR PREPARING N-CARBAMOYL-D-THIENYLGLYCINES

[75] Inventors: Hideaki Yamada, Kyoto; Satomi Takahashi, Kobe; Koji Yoneda, Amagasaki, all of Japan

[73] Assignee: Kanegafuchi Kagaku Kogyo Kabushiki Kaisha, Osaka, Japan

[*] Notice: The portion of the term of this patent subsequent to Jun. 13, 1995, has been disclaimed.

[21] Appl. No.: 18,876

[22] Filed: Mar. 9, 1979

[30] Foreign Application Priority Data

Mar. 15, 1978 [JP] Japan .................................. 53/30062

[51] Int. Cl.³ .............................................. C12P 17/00
[52] U.S. Cl. .................... 435/117; 435/106; 435/280; 435/828; 435/832; 435/840; 435/843; 435/863; 435/874; 435/826; 435/872; 435/886
[58] Field of Search ........................ 435/117, 280, 106

[56] References Cited

U.S. PATENT DOCUMENTS

| | | | |
|---|---|---|---|
| 3,198,804 | 8/1965 | Johnson et al. | 260/306.7 |
| 4,065,353 | 12/1977 | Cecere et al. | 435/129 |
| 4,094,741 | 6/1978 | Yamada et al. | 435/129 |

FOREIGN PATENT DOCUMENTS 53-6489 7/1978 Japan .

OTHER PUBLICATIONS

Nishimura et al., J. Chem. Soc. Japan, vol. 82, No. 12, 1688–1691 (1961).

*Primary Examiner*—Alvin E. Tanenholtz
*Attorney, Agent, or Firm*—Armstrong, Nikaido, Marmelstein & Kubovcik

[57] ABSTRACT

A process for preparing N-carbamoyl-D-(2-thienyl or 3-thienyl)glycine by subjecting 5-(2-thienyl or 3-thienyl)hydantoin to the action of a cultured broth, cells or treated cells of microorganisms having an ability of stereospecifically hydrolyzing the hydantoin ring. N-carbamoyl-D-(2-thienyl or 3-thienyl)glycine is a useful intermediate for the preparation of medicines and can be readily converted into D-(2-thienyl or 3-thienyl)glycine.

11 Claims, No Drawings

PROCESS FOR PREPARING N-CARBAMOYL-D-THIENYLGLYCINES

BACKGROUND OF THE INVENTION

The present invention relates to a process for preparing N-carbamoyl-D-(2-thienyl or 3-thienyl)glycine which can be readily converted into D-(2-thienyl or 3-thienyl)glycine, and more particularly to a process for preparing N-carbamoyl-D-(2-thienyl or 3-thienyl)glycine by biochemically hydrolyzing 5-(2-thienyl or 3-thienyl)hydantoin by employing intracellular enzymes of microorganisms.

The present inventors already found that N-carbamoyl-D-(phenyl or substituted phenyl)glycines can be prepared by subjecting 5-(phenyl or substituted phenyl)hydantoins to the action of microbial enzymes (U.S. Pat. No. 4,094,741), and also that N-carbamoyl-D-α-amino acids can be prepared from 5-substituted hydantoins corresponding to natural amino acids or their substituted derivatives in the same manner as above (U.S. patent application Ser. No. 862,853).

It is well known that D-thienylglycines are an available intermediate for the preparation of antibiotics such as semi-synthetic penicillins and semi-synthetic cephalorsporins. As a process for preparing D-thienylglycine, there is reported in Journal of the Chemical Society of Japan, Vol. 82, No. 12, 1688–1691 (1961) a process in which DL-thienylglycine is prepared from thiophene aldehyde by Streker method and is subjected to N-chloroacetylation, and after subjecting only the L-form to the dechloroacetylation by employing acylase extracted from kidney of a pig the residual N-chloroacetyl-D-thienylglycine is hydrolyzed. A process is also known in which acylase obtained from microorganisms is employed in the optical resolution of N-chloroacetyl-DL-thienylglycine, as disclosed in Japanese Unexamined Patent Publication No. 6489/1978. In U.S. Pat. No. 3,198,804, there is disclosed a process in which DL-thienylglycine is produced by hydrolyzing 5-thienylhydantoin synthesized from thiophene aldehyde and is then subjected to optical resolution by employing d-10-camphorsulfonic acid. However, these processes require the use of the expensive acylase or require steps of recovering and racemizing a residual unnecessary optical isomer.

SUMMARY OF THE INVENTION

Accordingly, it is an object of the present invention to provide a process for preparing a precursor of D-thienylglycine useful as an intermediate for the synthesis of medicines.

Another object of the invention is to provide a process for easily and economically preparing N-carbamoyl-D-thienylglycines in good yields by employing microbial enzymes.

These and other objects of the invention will become apparent from the description hereinafter.

The present invention provides a process for preparing N-carbamoyl-D-(2-thienyl or 3-thienyl)glycine by subjecting 5-(2-thienyl or 3-thienyl)hydantoin to the action of an enzyme which is in the form of a cultured broth containing microorganisms or the separated cells of the microorganisms in an aqueous medium, the enzyme being capable of hydrolyzing 5-(2-thienyl or 3-thienyl)hydantoin so as to substantially produce only D-form of N-carbamoyl(2-thienyl or 3-thienyl)glycine, and recovering N-carbamoyl-D-(2-thienyl or 3-thienyl)glycine from the medium.

DETAILED DESCRIPTION

The reaction according to the process of the present invention is illustrated as follows:

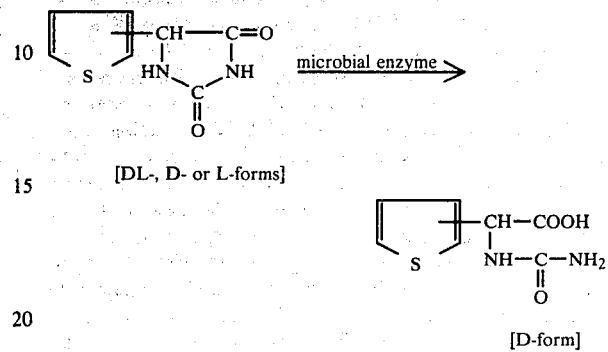

The intracellular enzymes of microorganisms used in the present invention selectively hydrolyze only D-form of 5-thienylhydantoins. Since 5-thienylhydantoins which are optically active easily racemize in an aqueous medium of pH 7 to 10, the D-form of 5-thienylhydantoins is always supplied in the reaction system by a fast racemization of the unhydrolyzed L-form, while the D-form is consumed. Therefore, any of DL-, D- and L-forms of 5-thienylhydantoins can be employed in the present invention, and only D-form of N-carbamoyl-thienylglycines can be obtained as a product. Thus, according to the present invention, DL-5-thienylhydantoins can be almost quantitatively converted into the D-form of N-carbamoylthienylglycines by employing microbial enzymes which can be readily and inexpensively obtained. Moreover, the thus obtained N-carbamoyl-D-thienylglycines can be readily converted into D-thienylglycines in good yields, for instance, by reacting them with nitrous acid. Accordingly, the present invention may also provide an industrially available process for preparing D-thienylglycines, which does not require any process step of recovering and racemizing an unnecessary optical isomer as in conventional processes.

Any of DL-, D- and L-forms of 5-thienylhydantoins can be employed in the present invention as the starting material, and the DL-form obtained by a chemical synthesis is usually employed. Also, both 5-(2-thienyl)hydantoin and 5-(3-thienyl)hydantoin are usable in the present invention. DL-5-(2-thienyl or 3-thienyl)hydantoin is prepared, for instance, by reacting 2-thiophene or 3-thiophene aldehyde with sodium cyanide and ammonium bicarbonate according to a Bucherer-Berg's method.

The microorganisms employed in the present invention are those having an ability of stereospecifically hydrolyzing the hydantoin ring of 5-thienylhydantoins to cleave, and are selected by examining wild strains present in nature, strains deposited in public organizations and microorganisms obtained by artificial mutation from those strains for the presence of the above ability. The expression "ability of stereospecifically hydrolyzing the hydantoin ring" as used herein means an ability to hydrolyze the hydantoin ring of 5-thienylhydantoins so as to substantially produce only D-form of N-carbamoylthienylglycines. As a method of examining for this ability, for instance, a method as stated below may be employed:

First, cells are collected by subjecting 2 ml. of a cultured broth of the microorganism to centrifugation, and then washed with 2 ml. of a 0.9% by weight saline water. Again, cells are collected by centrifugation. The thus obtained cells (wet weight: 40 to 200 mg.) are added to 2 ml. of a 0.5 to 10% by weight aqueous solution or suspension of DL-5-thienylhydantoins. The reaction is then carried out at pH 7 to 10 at 30° to 40° C. for 10 to 40 hours. After the completion of the reaction, a concentrated hydrochloric acid solution of p-dimethylaminobenzaldehyde is added to the reaction mixture to develop a color, and the resulting color-developed reaction mixture is subjected to centrifugation to remove insoluble substances such as cells. The amount of the produced N-carbamoylthienylglycines is then determined by measuring the absorbance of the resulting supernatant liquid at 430 nm. With respect to the strain showing the relatively high conversion, the hydrolysis reaction of 5-thienylhydantoins is again carried out on a large scale, and the produced N-carbamoylthienylglycines are isolated. Such strains as are confirmed to produce the D-form of N-carbamoylthienylglycines are adopted as the microorganisms employed in the present invention.

The microorganisms employed in the present invention are those passing the above examination, being selected from bacteria, actinomycetes, molds, yeasts and deuteromycetes. According to the research of the present inventors, such microorganisms can be found in a very wide range of the genus from the standpoint of taxonomy. Microorganisms as disclosed in U.S. Pat. No. 4,094,741 and U.S. patent application Ser. No. 862,853 are usable in the present invention. For instance, microorganisms showing a specially high activity to 5-thienylhydantoins are found in genera Aerobacter, Agrobacterium, Bacillus, Brevibacterium, Corynebacterium, Microbacterium and Pseudomonas which belong to bacteria, and in genera Actinomyces, Mycobacterium, Nocardia and Streptomyces which belong to actinomycetes.

The process of the present invention utilizes the catalytic action of an intracellular enzyme in the form of the cells or treated cells of microorganisms. The enzyme can be formed and accumulated in cells by culturing a microorganism on a usual culture medium containing natural nutrients in a conventional manner. Although the culture is usually effected in a liquid medium, solid surface culture may also be employed. In general, carbon and nitrogen sources which microorganisms can assimilate and inorganic salts and other nutrients essential for the growth of the microorganisms are included in the culture medium. Preferably, various kinds of pyrimidine bases or their derivatives or various kinds of hydantoin compounds are added to the culture medium in an amount of 0.05% to 0.3% by weight to adaptively enhance the desired enzyme activity. Pyrimidine bases such as uracil, cytocine and tymine and their derivatives such as dihydrouracil and dihydrotymine show a high enzyme-inducing effect. As the hydantoin compound, hydantoin and DL-5-methylhydantoin are desirably employed. Among them, uracil is practically the most preferable emzyme-inducing substrate common to many microorganisms. The culture conditions are selected from the temperature range of 20° to 85° C. and pH range of 4 to 11 in accordance with the optimum growth conditions of the employed strain, and usually the microorganisms are cultured at a temperature of 20° to 40° C. at a pH of 5 to 9 for 10 to 75 hours. During the culture, the growth of the microorganism may be accelerated by aeration and agitation.

The thus cultured microorganisms are employed in the form of the cultured broth, cells or treated cells in the hydrolysis of 5-thienylhydantoins. In many cases, the reaction can be conducted by employing the cultured broth containing the cells of microorganism as it is. However, in cases where components in the cultured broth are an obstacle to the reaction or where it is desired to increase the amount of enzyme, cells separated from the cultured broth are employed. Although the objects of the invention can be sufficiently attained by employing the intact cells, the cells may be employed in the form of the dried cells, for example, lyophilized cells and acetone powder, for the convenience of storage or handling. Also, the cells may be employed in the form of the treated cells, for example, crushed cells and cellular extract. Further, these cells and treated cells may be immobilized in a conventional manner.

The reaction substrate, i.e. 5-thienylhydantoins are usually admixed with the cultured broth, cells or treated cells in an aqueous medium to make the enzymes act catalytically on the substrate. The concentration of 5-thienylhydantoins is selected from 5% to 30% by weight. Although 5-thienylhydantoins cannot be often completely dissolved in an aqueous medium, this is not an obstacle to the reaction since 5-thienylhydantoins are progressively dissolved in the aqueous reaction medium with the progress of the reaction.

The actual substrate for the microbial enzymes employed in the present invention is D-form of 5-thienylhydantoins, and only D-form is selectively hydrolyzed to be converted into N-carbamoyl-D-thienylglycines. However, since 5-thienylhydantoins keep the racemization equilibrium in the reaction system, the unhydrolyzed L-form is converted into the D-form with the consumption of the D-form, and as a result, the D-form is always supplied in the reaction system. The L-form is not actual substrate, but can be regarded as the indirect substrate, since the racemization reaction proceeds in parallel with the enzymatic reaction. Therefore, any of DL-, D- and L-forms of 5-thienylhydantoins can be employed as the starting material.

When carrying out the stereospecific hydrolysis reaction of 5-thienylhydantoins in an aqueous reaction medium, the reaction mixture is usually maintained at pH 7 to 10, preferably 8 to 9. At this pH range, the desired product can be obtained in high yields by employing microorganisms having a high activity. When pH is lower than 7, the reaction rate is very low. Also, when pH is higher than 10, a side reaction may occur. At pH 7 to 10 the conversion rate of 5-thienylhydantoins into N-carbamoyl-D-thienylglycines is remarkably increased, since the optimum pH of the microbial enzymes employed in the invention is near 8 to 9, the solubility of the substrate increases with increasing pH and the racemization of the hydantoin ring is effectively accelerated under an alkaline condition. With the progress of the reaction the pH of the reaction system may decrease and, therefore, it is preferable to add at an appropriate time a neutralizing agent such as ammonia, caustic soda, caustic potash or sodium carbonate to the reaction system to maintain it at the optimum pH. Also, as occasion demands, an organic solvent and a surface active agent may be added to the reaction medium.

The hydrolysis reaction is carried out at a temperature suitable to the utilized microbial enzyme, usually at a temperature of 20° to 85° C. The reaction time varies depending on the activity of the employed microorganism and the reaction temperature, and is usually selected from 1 to 50 hours.

The N-carbamoylthienylglycines produced by the hydrolysis reaction are usually employed as they are, without isolating them, in a subsequent reaction step for converting them into the D-thienylglycines. When it is desired to isolate the produced N-carbamoylthienylglycines from the reaction mixture, usual methods such as a method using an anion-exchange resin are applicable.

The N-carbamoyl-D-thienylglycines obtained by the process of the present invention can be readily converted into D-thienylglycines, for instance, by reacting them with nitrous acid. This decarbamoylation is carried out in the presence of an acid, which accelerates the reaction rate of the decarbamoylation. As the acid, inorganic acids such as mineral acids and organic acids, e.g. formic acid, p-toluene-sulfonic acid, and the like are employed. Strong mineral acids such as hydrochloric acid and sulfuric acid are preferred. The reaction is usually carried out in an aqueous medium. Water or an aqueous mixed solvent such as a water-acetic acid or a water-alcohol mixed solvent is employed, but a water-acetic acid is the most preferable solvent. Nitrous acid is employed in the form of nitrosylsulfuric acid or sodium nitrite or potassium nitrite under the condition that the reaction system is maintained acidic. The D-thienylglycines formed are isolated using an ion-exchange resin or by the concentration of the reaction mixture followed by the neutralization with an alkali. The D-thienylglycines, particularly D-(2-thienyl)glycine is an important intermediate for the preparation of medicines such as semi-synthetic penicillins and semi-synthetic cephalosporins, and can be advantageously prepared on an industrial scale by utilizing the process of the present invention.

The present invention is more particularly described and explained by means of the following Examples, in which all % are by weight unless otherwise noted. These Examples are intended to illustrate the invention and not to be construed to limit the scope of the invention.

Also, the microorganisms employed in the following Examples are all previously known, and strains marked with IAM, IFO or ATCC are those deposited in the following depositories under the shown catalogue numbers.

IAM: Institute of Applied Microbiology, the University of Tokyo (Japan)
IFO: Institute for Fermentation, Osaka (Japan)
ATCC: American Type Culture Collection (U.S.A.)

EXAMPLE 1

A liquid culture medium of pH 7.0 containing the following components was prepared, and 10 ml. portions thereof were separately placed in test tubes with cotton stoppers and were steam-sterilized at 120° C. for 15 minutes.

| Medium Components | |
| --- | --- |
| Meat extract | 0.5% |
| Yeast extract | 0.5% |
| Polypeptone | 1.0% |
| NaCl | 0.15% |

| Medium Components | |
| --- | --- |
| Uracil | 0.1% |

Each microorganism shown in Table 1 which had been previously cultured on bouillon agar slants at 30° C. for 24 hours, was inoculated into the culture medium in each test tube with a platinum loop, and then cultured at 33° C. for 16 hours with shaking. Intact cells were separated from 4 ml. each of the resulting cultured broths by centrifugation and washed with 4 ml. of a 0.9% saline water. The cells were collected again by centrifugation, and were employed as a component of the mixture described below.

Mixture Components (1) 4.0 ml. of aqueous substrate solution (pH 8.5) in concentration of 54.9 mM (1.0 w/v %) which was prepared by dissolving DL-5-(2-thienyl)hydantoin in a 0.05 M $NaHCO_3$-$Na_2CO_3$ buffer solution
(2) the above-mentioned intact cells obtained from 4.0 ml. of cultured broth A ground stopper test tube was charged with a mixture of the above components (1) and (2) in which cells were well suspended, and the reaction was then carried out at 37° C. for 5.0 hours with mild shaking. The reaction was stopped by immersing the test tube in ice water, and the reaction mixture was diluted with pure water to 10 times the original volume. To 40 ml. of the diluted reaction mixture were added 2.0 ml. of a 20% aqueous solution of trichloroacetic acid, 1.0 ml. of a 10% solution of p-dimethylaminobenzaldehyde in 12 N hydrochloric acid. The liquid developed to yellow color was centrifuged to remove insoluble substances and then subjected to the colorimetric determination of N-carbamoyl-2-(2-thienyl)glycine by measuring the absorbance at 430 nm. These reaction and determination procedures were repeated for each microorganism.

The amounts of N-carbamoyl-2-(2-thienyl)glycine produced in the reaction mixtures and the conversions from DL-5-(2-thienyl)hydantoin are shown in Table 1.

Table 1

| Strain | Amount of N-carbamoyl-2-(2-thienyl)-glycine µ mole/ml. | Conversion mole % |
| --- | --- | --- |
| Aerobacter cloacae IAM 1221 | 18.8 | 34.2 |
| Agrobacterium rhizogenes IFO 13259 | 20.7 | 37.7 |
| Corynebacterium sepedonicum IFO 3306 | 40.2 | 73.2 |
| Corynebacterium erythrogenes IFO 12974 | 3.1 | 5.6 |
| Microbacterium flavum ATCC 10340 | 2.8 | 5.1 |
| Mycobacterium smegmatis ATCC 607 | 35.0 | 63.8 |
| Nocardia corallina IFO 3338 | 31.7 | 57.7 |
| Brevibacterium incertum IFO 12145 | 6.0 | 10.9 |
| Bacillus sphaericus IFO 3525 | 1.2 | 2.2 |
| Pseudomonas striata IFO 12996 | 40.0 | 72.9 |
| Pseudomonas aeruginosa IFO 3445 | 40.2 | 73.2 |
| Control | 0.0 | 0 |

EXAMPLE 2

A liquid culture medium of pH 7.0 containing the following components was prepared, and 10 ml. portions thereof were placed in test tubes with cotton stoppers and were steam-sterilized at 120° C. for 20 minutes.

| Medium Components | |
|---|---|
| Glucose | 2.0% |
| Soybean meal | 1.0% |
| Yeast extract | 0.25% |
| (NH4)2SO4 | 0.10% |
| CaCO3 | 0.5% |
| K2HPO4 | 0.4% |
| DL-5-(2-methylthioethyl)hydantoin | 0.1% |

Each microorganism shown in Table 2 which had been previously cultured on a Bennett's agar slant at 28° C. for 72 hours, was inoculated into the liquid culture medium in the test tube with a platinum loop and cultured at 28° C. for 44 hours with shaking. Washed intact cells were obtained by treating 40 ml. of the obtained cultured broth in the same manner as in Example 1. By removing each of the thus obtained cells, mixtures having the same composition as in Example 1 were prepared and the reaction was carried out at 37° C. for 20 hours with mild shaking. The amounts of N-carbamoyl-2-(2-thienyl)glycine produced in the reaction mixtures and the conversions from DL-5-(2-thienyl)hydantoin were obtained in the same manner as in Example 1.

The results are shown in Table 2.

Table 2

| Strain | Amount of N-carbamoyl-2-(2-thienyl)-glycine μ mole/ml. | Conversion mole % |
|---|---|---|
| Actinomyces griseoruber IFO 12872 | 3.7 | 6.7 |
| Streptomyces aureus IFO 3175 | 16.1 | 29.3 |
| Streptomyces flaveolus IFO 3408 | 13.0 | 23.7 |
| Streptomyces viridochromogenus IFO 3113 | 4.9 | 8.9 |
| Streptomyces griseus ATCC 10137 | 0.9 | 1.6 |
| Control | 0.0 | 0 |

EXAMPLE 3

The following liquid culture mediums (A) and (B) were prepared, and 300 ml. portions thereof were separately placed in 2 liter shaking flasks and steam-sterilized at 120° C. for 15 minutes.

| Culture Medium (A) | | Culture Medium (B) | |
|---|---|---|---|
| Meat extract | 2.0% | Meat extract | 0.5% |
| Glycerol | 0.6% | Yeast extract | 0.5% |
| Uracil | 0.1% | Polypeptone | 1.0% |
| pH | 6.5 | NaCl | 0.15% |
| | | Uracil | 0.1% |
| | | pH | 7.0 |

Each microorganism shown in Table 3 which had been previously cultured on a bouillon agar slant at 30° C. for 24 hours, was suspended in 10 ml. of a sterilized 0.9% saline water. The obtained suspension was inoculated in the culture medium (A) or (B), and was cultured at 33° C. for 18 hours with shaking. Cells were separated from each resulting cultured broth by centrifugation and washed with 150 ml. of a 0.9% saline water. The cells were collected again by centrifugation, and then suspended into 100 ml. of a 0.9% saline water. Each thus obtained cell suspension was employed as a component of the mixture described below.

Mixture Components (1) 100 ml. of aqueous substrate suspension containing 15% of DL-5-(2-thienyl)hydantoin which was adjusted to pH 8.5

(2) 50 ml. of cell suspension

A 300 ml. four-necked round bottom flask was charged with the above components (1) and (2), and the reaction was then carried out at 37° C. for 18 hours in a nitrogen stream with stirring. During the reaction the reaction system was successively adjusted to pH 8.5 by employing 2.5 N NaOH solution. After the completion of the reaction, the reaction mixture was adjusted to pH 5.0 and was centrifuged to remove insoluble substances. A part of the obtained supernatant liquid was taken out and the produced N-carbamoyl-2-(2-thienyl)glycine was colorimetrically determined in the same manner as in Example 1. The remaining supernatant liquid was adjusted to pH 1.5 to 2 by conc. hydrochloric acid to precipitate N-carbamoyl-2-(2-thienyl)glycine. The precipitate was filtered and recrystallized from an ethanol-water mixed solvent to give N-carbamoyl-2-(2-thienyl)glycine of high purity. The amount and specific rotatory power of the thus obtained crystalline N-carbamoyl-2-(2-thienyl)glycine were measured (condition of measuring specific rotatory power: c=1, 1 N NH4Cl). The above reaction and determination procedures were repeated for each microorganism.

The results of the amounts of N-carbamoyl-2-(2-thienyl)glycine produced in reaction system and the obtained N-carbamoyl-2-(2-thienyl)glycine, the conversion from DL-5-(2-thienyl)hydantoin and the specific rotatory power are shown in Table 3.

It was confirmed from the results of measurement of the specific rotatory power that all the obtained N-carbamoyl-2-(2-thienyl)glycine were D-form. Also, the results of the elemental analysis and infrared spectrum were theoretically reasonable. Further, it was observed from a silica-gel thin layer chromatogram (solvent: n-butanol/acetic acid/water=4/1/1) that the obtained product was highly pure.

Table 3

| Strain | Medium | Amount of N-carbamoyl-2-(2-thienyl)glycine produced in reaction system μ mole/ml. | Conversion mole % | Amount of obtained crystal g. | Specific rotatory power $[\alpha]_D^{25}$ |
|---|---|---|---|---|---|
| Aerobacter cloacae IAM 1221 | A | 77 | 93 | 9.8 | −97.0 |
| Agrobacterium rhizogenes IFO 13259 | B | 46 | 56 | 4.1 | −95.4 |
| Corynebacterium sepedonicum IFO 3306 | B | 68 | 83 | 9.8 | −97.0 |
| Mycobacterium smegmatis ATCC 607 | B | 70 | 85 | 7.6 | −92.1 |
| Pseudomonas striata IFO 12996 | A | 82 | 100 | 10.5 | −97.7 |

Each thus obtained N-carbamoyl-2-(2-thienyl)glycine was subjected to decarbamoylation by reacting it with nitrous acid to give 2-(2-thienyl)glycine as follows: To a mixture of 5.0 g. of N-carbamoyl-D-(2-thienyl)glycine, 10 ml. of conc. HCl and a 100 ml. of a 50% aqueous acetic acid, 8.6 g. of a 20% aqueous solution of NaNO₂ was added at 10° C. with stirring. After the completion of adding NaNO₂, the reaction was carried out at 10° C. for 2 hours. The formed D-2-(2-thienyl)glycine was isolated by adsorption on an anion-exchange resin (commercially available under the registered trademark "Amberlite IR-120B" made by Rohm & Haas Co.) followed by elution with ammonia water. The fraction obtained was concentrated and neutralized with hydrochloric acid. D-2-(2-thienyl)glycine was collected and recrystallized from an aqueous ethanol. The amount of the obtained D-2-(2-thienyl)glycine was 2.9 g.

The specific rotatory power of the products was $[\alpha]_D^{25} = -73.0$ to $-74.2$ (c=1, H₂O) and it was confirmed that the products were D-2-(2-thienyl)glycine of high purity.

What we claim is:

1. A process for preparing N-carbamoyl-D-(2-thienyl or 3-thienyl)glycine which comprises subjecting 5-(2-thienyl or 3-thienyl)hydantoin to the action of an enzyme which is in the form of a cultured broth containing microorganisms or the separated cells of said microorganisms in an aqueous medium, said enzyme being capable of hydrolyzing 5-(2-thienyl or 3-thienyl)hydantoin so as to substantially produce only D-form of N-carbamoyl(2-thienyl or 3-thienyl)glycine, and recovering N-carbamoyl-D-(2-thienyl or 3-thienyl)glycine from the medium.

2. The process of claim 1, wherein said aqueous medium is maintained at pH 7 to 10.

3. The process of claim 1, wherein said microorganisms are selected from microorganisms belonging to genus Aerobacter, Agrobacterium, Bacillus, Brevibacterium, Corynebacterium, Microbacterium, Pseudomonas, Actinomyces, Mycobacterium, Nocardia and Streptomyces.

4. The process of claim 1, wherein said cells are intact cells or dried cells.

5. The process of claim 1, wherein said cells are crushed cells or in the form of a cellular extract.

6. The process of claim 1, wherein said cells are immobilized.

7. The process of claim 1, wherein said microorganisms are those cultured in a culture medium containing a pyrimidine base or its derivative which enhances the ability of stereospecifically hydrolyzing the hydantoin ring.

8. The process of claim 1, wherein said 5-(2-thienyl or 3-thienyl)hydantoin is the DL-form.

9. A process for preparing D-(2-thienyl or 3-thienyl)glycine which comprises subjecting 5-(2-thienyl or 3-thienyl)hydantoin to the action of an enzyme which is in the form of a cultured broth containing microorganisms or the separated cells of said microorganisms in an aqueous medium, said enzyme being capable of hydrolyzing 5-(2-thienyl or 3-thienyl)hydantoin so as to substantially produce only D-form of N-carbamoyl(2-thienyl or 3-thienyl)glycine, reacting the resulting N-carbamoyl-D-(2-thienyl or 3-thienyl)glycine with nitrous acid in the presence of an acid, and recovering D-(2-thienyl or 3-thienyl)glycine.

10. The process of claim 9, wherein said aqueous medium is maintained at pH 7 to 10.

11. The process of claim 9, wherein said acid is an inorganic acid.

* * * * *